(12) United States Patent
Chen et al.

(10) Patent No.: US 10,267,883 B2
(45) Date of Patent: Apr. 23, 2019

(54) SYSTEM AND METHOD FOR MOTION RESOLVED MRI

(71) Applicant: Siemens Healthcare GmbH, Erlangen (DE)

(72) Inventors: Xiao Chen, Somerset, NJ (US);
Mariappan S. Nadar, Plainsboro, NJ (US); Marcel Dominik Nickel, Herzogenaurach (DE); Boris Mailhe, Plainsboro, NJ (US); Qiu Wang, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 361 days.

(21) Appl. No.: 15/361,670

(22) Filed: Nov. 28, 2016

(65) Prior Publication Data

US 2017/0168129 A1 Jun. 15, 2017

Related U.S. Application Data

(60) Provisional application No. 62/266,511, filed on Dec. 11, 2015.

(51) Int. Cl.
*G01R 33/563* (2006.01)
*G01R 33/48* (2006.01)
(Continued)

(52) U.S. Cl.
CPC ........ *G01R 33/56308* (2013.01); *A61B 5/004* (2013.01); *A61B 5/055* (2013.01);
(Continued)

(58) Field of Classification Search
None
See application file for complete search history.

(56) References Cited

U.S. PATENT DOCUMENTS 7,408,347 B2 8/2008 Mistretta et al.
8,290,566 B2 * 10/2012 Iwadate ................ A61B 5/055
324/318

(Continued)

FOREIGN PATENT DOCUMENTS

JP 2009533128 A 9/2009
KR 20130086321 A 8/2013
(Continued)

OTHER PUBLICATIONS

Wiesner, Stefan, Respiration Monitoring and Tomographic Reconstruction Towards 4D Cone Beam CT, Technical Report, CAIMR TR-2007-1, Sep. 2007, 62 pages.
(Continued)

*Primary Examiner* — Jermele M Hollington

(57) ABSTRACT

A method comprises acquiring navigation data during navigation scans at each of a plurality of points in time. A plurality of magnetic resonance imaging (MRI) k-space data corresponding to an imaged object are acquired at the plurality of points in time using Cartesian sampling, the k-space data including at least two spatial dimensions, a time. The respective motion state for each of the k-space data are computed based on the navigation data. At least one image is reconstructed from the plurality MRI k-space data using k-space data corresponding to at least two motion states and the same point in time to reconstruct the at least one image.

17 Claims, 11 Drawing Sheets

(51) Int. Cl.

| | |
|---|---|
| *A61B 5/055* | (2006.01) |
| *A61B 5/00* | (2006.01) |
| *G01R 33/56* | (2006.01) |
| *G06T 7/00* | (2017.01) |
| *G06T 11/00* | (2006.01) |
| *G01R 33/567* | (2006.01) |
| *G01R 33/485* | (2006.01) |

(52) U.S. Cl.
CPC .......... *A61B 5/4244* (2013.01); *A61B 5/7207* (2013.01); *A61B 5/7225* (2013.01); *G01R 33/482* (2013.01); *G01R 33/4818* (2013.01); *G01R 33/56* (2013.01); *G01R 33/5601* (2013.01); *G01R 33/5608* (2013.01); *G01R 33/5635* (2013.01); *G01R 33/5676* (2013.01); *G06T 7/0012* (2013.01); *G06T 11/003* (2013.01); *A61B 2576/02* (2013.01); *G01R 33/485* (2013.01); *G01R 33/5607* (2013.01); *G06T 2207/10088* (2013.01); *G06T 2207/30056* (2013.01)

(56) References Cited

U.S. PATENT DOCUMENTS

| | | | |
|---|---|---|---|
| 2007/0156044 | A1 | 7/2007 | Mistretta et al. |
| 2009/0270720 | A1* | 10/2009 | Iwadate .............. G01R 33/5676 600/413 |
| 2012/0146641 | A1 | 6/2012 | Hu et al. |
| 2012/0243756 | A1* | 9/2012 | Samsonov ....... G01R 33/56509 382/131 |
| 2013/0181712 | A1* | 7/2013 | Sutton .............. G01R 33/56341 324/314 |
| 2013/0281828 | A1* | 10/2013 | Stemmer ............ G01R 33/5673 600/413 |
| 2015/0073263 | A1 | 3/2015 | Gdaniec et al. |
| 2015/0212182 | A1* | 7/2015 | Nielsen ............ G01R 33/56509 702/191 |
| 2016/0146915 | A1 | 5/2016 | Mailhe et al. |
| 2016/0178720 | A1 | 6/2016 | Mailhe et al. |
| 2016/0247263 | A1 | 8/2016 | Mailhe et al. |
| 2016/0252596 | A1* | 9/2016 | Nielsen ................ G01R 33/482 324/309 |

FOREIGN PATENT DOCUMENTS

| | | |
|---|---|---|
| KR | 20130118828 A | 10/2013 |
| KR | 20150094528 A | 8/2015 |
| KR | 20150111259 A | 10/2015 |
| KR | 20150125543 A | 11/2015 |

OTHER PUBLICATIONS

Forman, Christoph et al, Reduction of Respiratory Motion Artifacts for Free-Breathing Whole-Heart Coronary MRA by Weighted Iterative Reconstruction, 2014 copy, pp. 1-32.

Huber, Armin, Navigator Echo-Based Respiratory Gating for Three-Dimensional MR Coronary Angiography: Results from Healthy Volunteers and Patients with Proximal Coronary Artery Stenoses, AJR;173, Jul. 1999, pp. 95-103.

Lustig, Michael et al, Compressed Sensing MRI, Technical Report No. 2007-3, Jul. 2007, pp. 1-40.

Lustig, Michael et al, Sparse MRI: The Application of Compressed Sensing for Rapid MR Imaging, Magnetic Resonance in Medicine 58:1182-1195 (2007), p. 1182-1195.

Chaari, Lotfi et al, Spatio-temporal wavelet regularization for parallel MRI reconstruction: application to functional MRI, Magnetic Resonance Materials in Physica, Biology and Medicine, Springer Verlag, 2014, 27 (6), pp. 41. <10.1007/s10334-014-0436-5>. <hal-01084324. Submitted on Dec. 29, 2014, 42 pages.

Purdon, Patrick L. et al, Locally Regularized Spatiotemporal Modeling and Model Comparison for Functional MRI, NeuroImage 14, 912-923 (2001).

Chartrand, Rick, Fast Algorithms for Nonconvex Compressive Sensing: MRI Reconstruction from Very Few Data, Los Alamos National Laboratory, 2009 IEEE International Symposium on Biomedical Imaging From Nano to Macro—ISBI 09, 4 pages.

Guerquin-Kern, M. et al, Wavelet-Regularized Reconstruction for Rapid MRI, 978-1-4244-3932-4/09, 2009 IEEE, ISBI 2009, pp. 193-196.

Antoniadis, Anestis et al, Regularization of Wavelet Approximations, Journal of the American Statistical Association, Sep. 2001, vol. 96, No. 455, Theory and Methods, p. 939-967.

Zhang, Tao et al, Fast 3D DCE-MRI with Sparsity and Low-Rank enhanced SPIRiT (SLR-SPIRiT), Proc. Intl. Soc. Mag. Reson. Med. 21 (2013), p. 2624.

Zhang, Tao et al, Fast 3D Free-breathing Abdominal Dynamic Contrast Enhanced MRI with High Spatiotemporal Resolution, Proc. Intl. Soc. Mag. Reson. Med. 22 (2014), p. 0332.

Katoh, Marcus et al, American Journal of Roentgenology, MRI of Coronary Vessel Walls Using Radial k-Space Sampling and Steady-State Free Precession Imaging, Jun. 2006, vol. 186, No. 6, Supplement 2, 14 pages.

Feng, Li et al, XD-GRASP: Golden-Angle Radial MRI with Reconstruction of Extra Motion-State Dimensions Using Compressed Sensing, Magn Reson Med. Feb. 2016; 75(2): 775-788. doi:10.1002/mrm.25665, pp. 1-25.

* cited by examiner

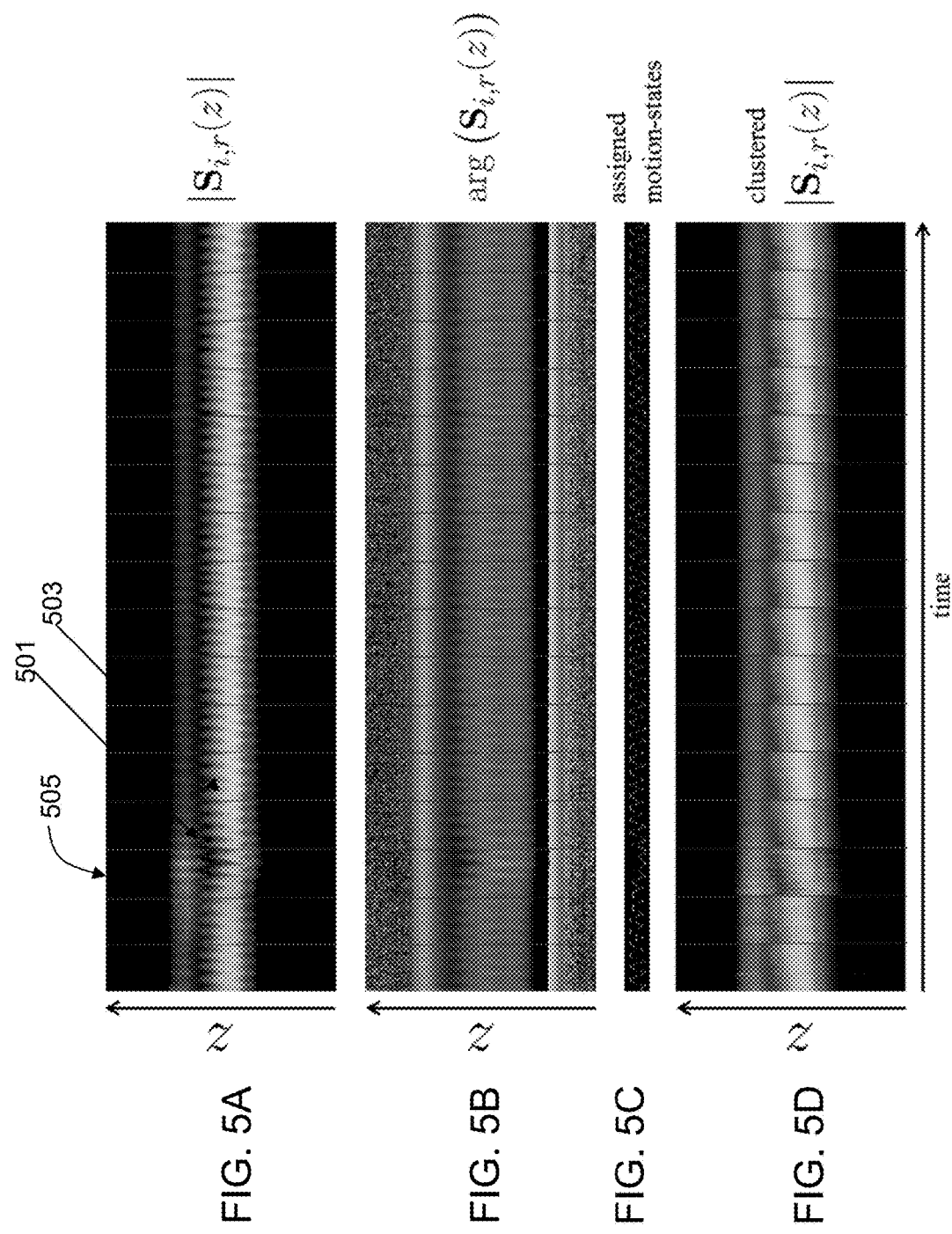

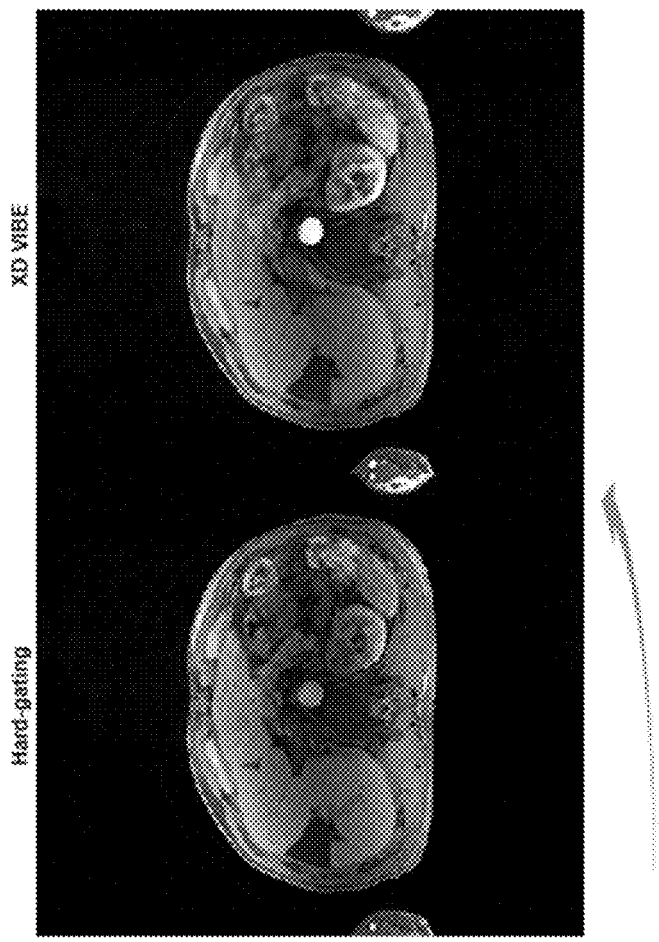
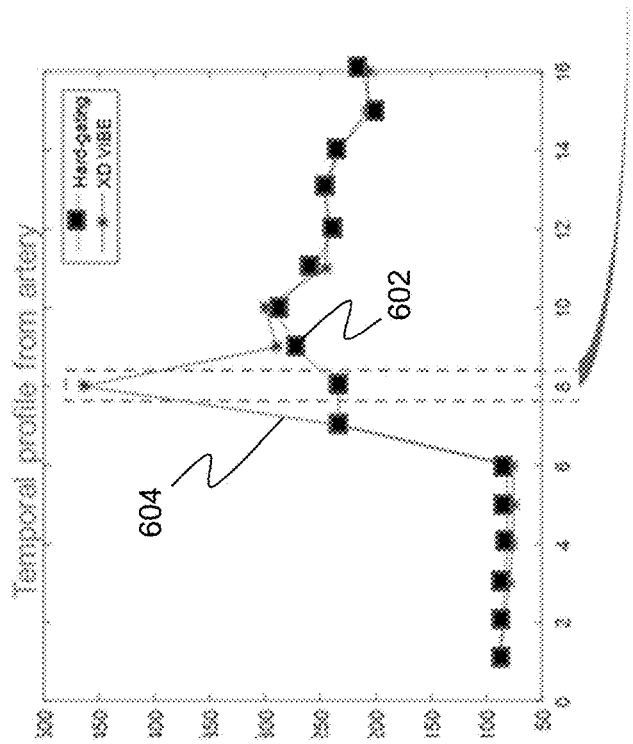
FIG. 6A
FIG. 6B

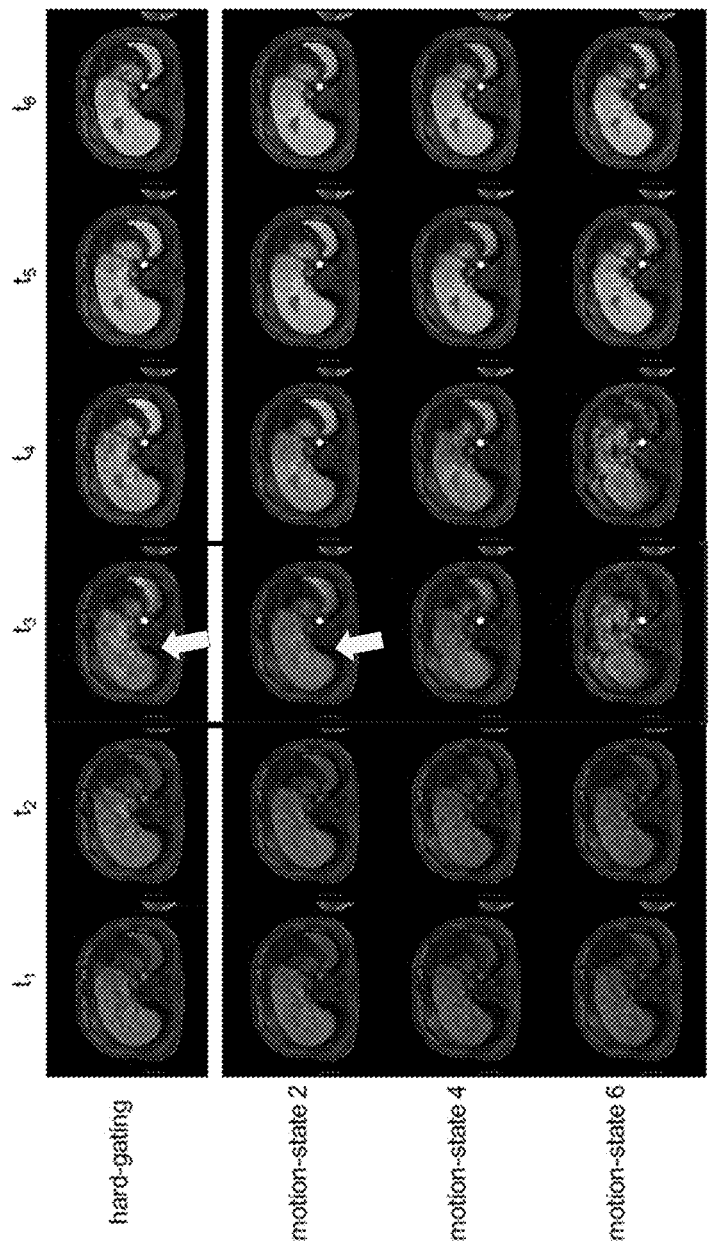

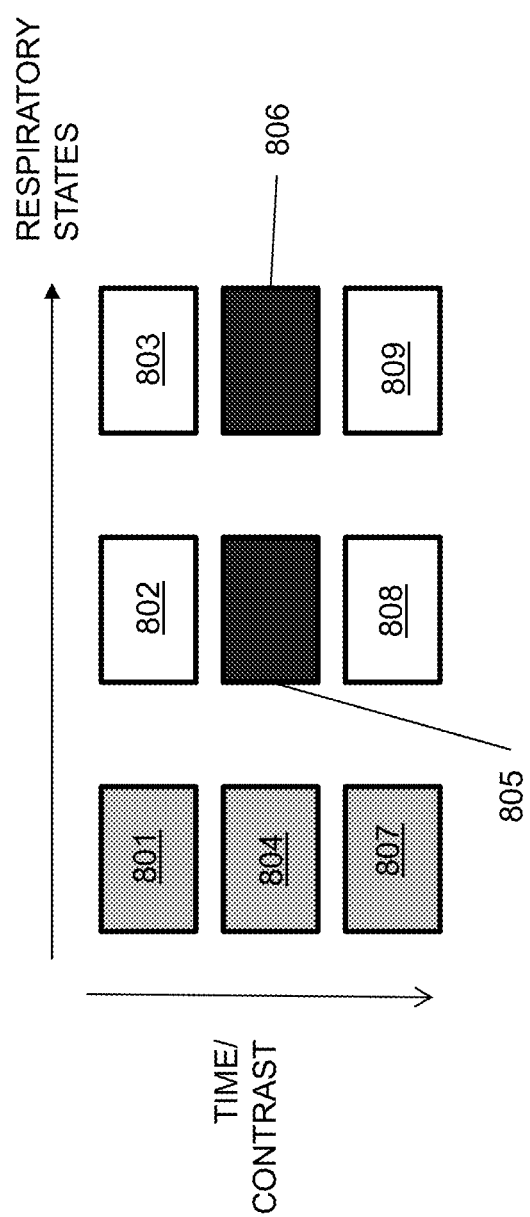

SYSTEM AND METHOD FOR MOTION RESOLVED MRI

This application claims the benefit of U.S. Provisional Patent Application No. 62/266,511, filed Dec. 11, 2015, which is expressly incorporated by reference herein in its entirety.

FIELD

This disclosure relates generally to methods, systems, and apparatuses for Magnetic Resonance Imaging (MRI) reconstruction.

BACKGROUND

Imaging inverse problems such as reconstruction, deblurring, super-resolution, inpainting, or denoising can be solved by assuming the target image is sparse in the wavelet domain. Orthogonal wavelet transforms are not shift-invariant; image features are processed differently depending on their position with respect to the wavelet grid, and this can result in blocking artifacts.

Techniques to solve the proximal operation performed during reconstruction have been developed, such as the utilization of an undecimated redundant wavelet transforms in conjunction with a nested inner algorithm inside the main solver (e.g. Chambolle-Pock or Dykstra inside FISTA).

Dynamic contrast-inhanced (DCE) MRI involves injection of a contrast agent (CA) into the patient and observing the dynamic intake of the CA into tissue at several different points in time using MRI. Image reconstruction methods apply multiple shifted wavelet transforms at each iteration, which incurs an extra computational cost of at least a factor of 2 per image dimension. Additionally, exact undecimated wavelet methods also store the wavelet coefficients of the image, which are larger than the image by a factor of two in every dimension. This becomes very large with large-dimension use-cases such as dynamic volumetric reconstruction (3D+T), motion-compensated imaging, multi-contrast imaging including flow or diffusion, etc.

SUMMARY

In some embodiments, a method comprises acquiring navigation signal data during navigation scans at each of a plurality of points in time. A plurality of magnetic resonance imaging (MRI) k-space data corresponding to an imaged object are acquired at the plurality of points in time using Cartesian sampling, the k-space data including at least two spatial dimensions, time and an assigned motion state. The respective motion state for each of the k-space data are computed based on navigation data. At least one image is reconstructed from the plurality MRI k-space data using k-space data corresponding to at least two motion states and the same point in time to reconstruct the at least one image.

In some embodiments, a magnetic resonance (MR) imaging device has a plurality of coils, and is configured to collect data representing an MR image from an object. A processor has a storage device for storing frequency components of the data acquired using a Cartesian acquisition strategy during acquisition of the frequency components, the processor programmed for acquiring navigation signal data during navigation scans at each of a plurality of points in time. A plurality of magnetic resonance imaging (MRI) k-space data corresponding to an imaged object are acquired at the plurality of points in time using Cartesian sampling, the k-space data including at least two spatial dimensions, a time, and a motion state. The respective motion state for each of the k-space data are computed based on navigation data. At least one image is reconstructed from the plurality MRI k-space data using k-space data corresponding to at least two motion states and the same point in time to reconstruct the at least one image.

In some embodiments, a non-transitory machine-readable storage medium encoded with computer program code, wherein when a processor executes the computer program code, the processor performs a method comprising acquiring navigation signal data during navigation scans at each of a plurality of points in time. A plurality of magnetic resonance imaging (MRI) k-space data corresponding to an imaged object are acquired at the plurality of points in time using Cartesian sampling, the k-space data including at least two spatial dimensions, a time. The respective motion state for each of the k-space data are computed based on navigation data. At least one image is reconstructed from the plurality MRI k-space data using k-space data corresponding to at least two motion states and the same point in time to reconstruct the at least one image.

BRIEF DESCRIPTION OF THE DRAWINGS

FIG. 5A shows the magnitude of the navigation signal over time.

FIG. 5B shows the phase of the navigation signal of FIG. 5A over time.

FIG. 5C shows the assigned motion states of the navigation signal of FIG. 5A over time.

FIG. 5D shows the acquired navigation signal of FIG. 5A clustered according to the assigned motion states.

FIG. 6A shows a comparison between the hard gating signal (squares) and the navigation signal (asterisks) over time.

FIG. 6B shows the images reconstructed from MR data using the hard gating signal and the 5D image data with extra time and motion state dimensions described herein.

FIG. 7A shows images reconstructed using the hard gating signal of FIG. 6A over six points in time.

FIG. 7B shows images reconstructed using the navigation signal of FIG. 6A over the same six points in time.

FIG. 8 is a schematic diagram of an XD Hybrid embodiment using data corresponding to extra motion states at critical points in time, and using data corresponding to a single motion state at other points in time.

DETAILED DESCRIPTION

Figure 1:
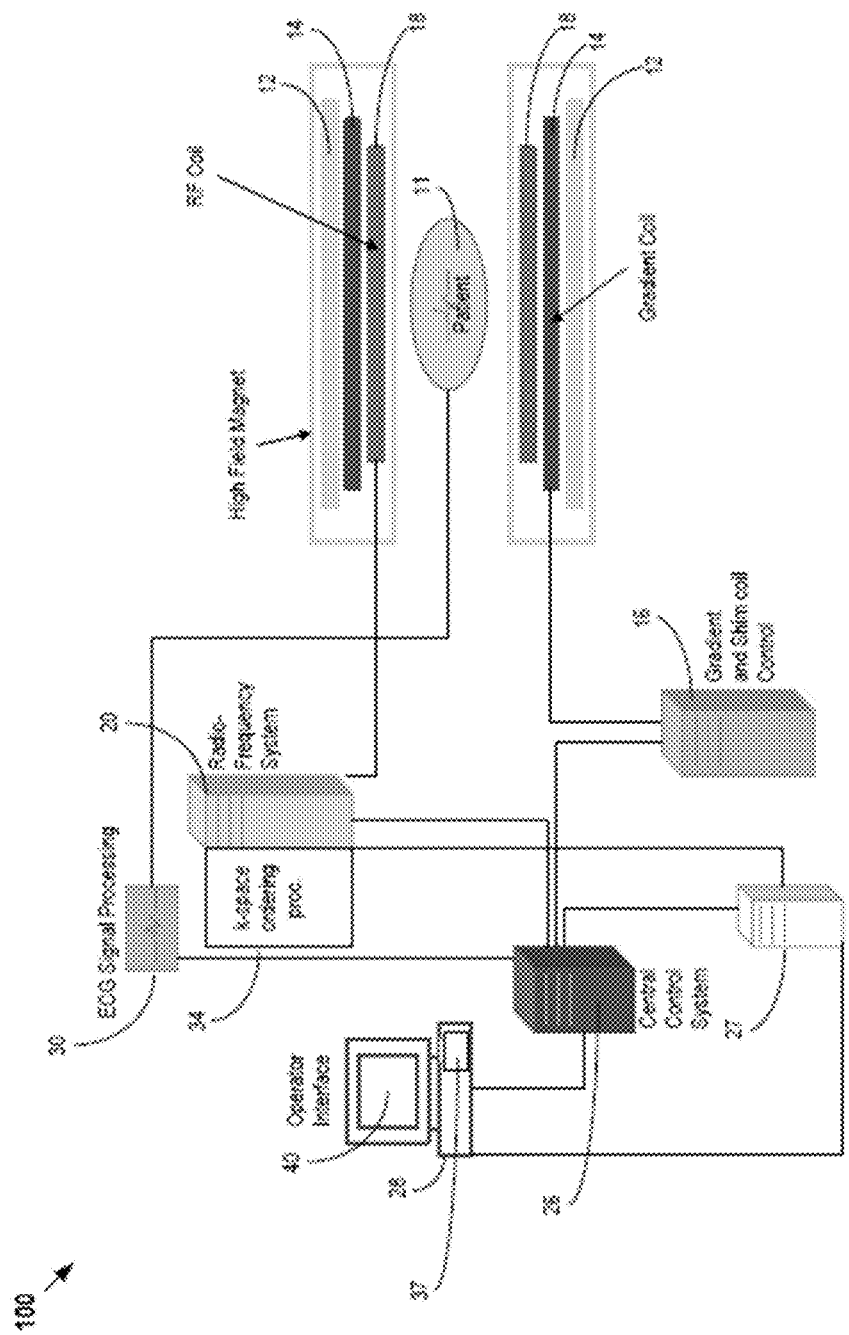
FIG. 1 shows a system for ordering acquisition of frequency domain components representing magnetic resonance (MR) image data for storage in a k-space storage array, as used by some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion.

This disclosure describes several embodiments directed at methods, systems, and apparatuses Magnetic Resonance Imaging (MRI) reconstruction using wavelet regularization. The techniques described herein may be applied to many if not all compressed sensing (CS) use-cases to provide an overall performance improvement without sacrificing image quality. U.S. Patent Application Publication No. US2016/0247263 by Mailhe et al. describes use of wavelets for regularization and reconstructing magnetic resonance images, and is incorporated by reference herein in its entirety. U.S. Patent Application Publication No. US2016/0146915 by Mailhe et al. describes a compressed sensing process for reconstructing magnetic resonance images, and is incorporated by reference herein in its entirety.

Some embodiments described herein use a Cartesian data acquisition method with a gating signal that is separate from spatial image data and time (perfusion state). The gating signal is representative of the motion state. Using Cartesian based acquisition simplifies computations and speeds up image processing. Some embodiments use the gating signal to resolve images collected in all motion states MRI scanning. Other embodiments use a hybrid approach, in which the gating signal is used to resolve images collected in all motion states at selected times (e.g., at certain perfusion states), and to only resolve images collected in a single or multiple selected motion states at all other times.

System Architecture

FIG. 1 shows a system 100 for ordering acquisition of frequency domain components representing Magnetic Resonance (MR) image data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-incoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-incoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset representing an MR image. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on display 40, for example.

Regularization

Many challenges in medical imaging such as reconstruction, denoising or super-resolution can be modeled mathematically as ill-posed linear inverse problems:

$$y = Ax + n \quad (1)$$

where the goal is to reconstruct an unknown signal y from partially incomplete data x that is corrupted by measurement noise n. The matrix A models the measurement system. In case of parallel MRI it is often modeled as A=FS with F representing the (partial) Fourier transform and S containing the coil sensitivities. Because the system is underdetermined, there exist infinitely many solutions to it and additional constraints to the solution are imposed. A standard approach to the estimator of Equation (1) is as follows:

$$\hat{x} = \underset{x}{\operatorname{argmin}} \frac{1}{2} \|y - Ax\|_2^2 + \lambda \Phi(x) \quad (2)$$

where $\frac{1}{2}\|y-Ax\|_2^2$ is the data fidelity term to enforce the solution to be close to the measurements and the function $\Phi(x)$ is called the regularizer with $\lambda > 0$ being the regularization parameter to balance the trade-off between the data fidelity and the regularization.

In some embodiments the solution is sparse with respect to a given basis, meaning having only few non-zero coefficients in that basis. Compressed sensing is a signal processing technique, in which the sparsity of a signal is exploited to recover it from far fewer samples than required by the Shannon-Nyquist sampling theorem. A popular approach in compressed sensing is a wavelet based framework and promoting sparsity in a given wavelet basis such as Haar. However, having the measure of non-zeroes $\|\cdot\|_0$ as a regularizer is NP-hard. Thus, in case of a wavelet based compressed sensing, the regularizer has often the form of $\|Wx\|_1$ and promotes sparsity with respect to the $l_1$-norm that is a convex approximation to the $l_0$ pseudo-norm. Here W represents a wavelet transform. In general, W can be any linear operator depending on the underlying problem. For example, for MRI reconstruction, some embodiments use an undecimated wavelet transform due to its translation invariance. However, the choice of algorithms to solve the optimization problem depends on the underlying regularizer. An efficient algorithm to solve Equation (1) is the iterative shrinkage/thresholding algorithm (ISTA), which is a special case of so called forward-backward splitting algorithms. A forward-backward splitting algorithm splits the problem into functions $f_1=\frac{1}{2}\|y-Ax\|_2^2$ and $f_2=\lambda \Phi(x)$ and uses them individually. Since $f_2$ is often non-smooth it is processed via its proximity operator. The iterative scheme takes a gradient step on the function $f_1$ (forward step) and evaluates the proximity operator of function $f_2$ at that new point (backward step). Redundant wavelet transforms can be handled by using a Chambolle-Pock type algorithm for the proximal step. However, from a practical perspective, using orthogonal wavelets have the advantage of reducing the memory consumption and therefore faster processing times.

Given a function g(x), the proximal operator is the solution of the minimization problem:

$$\underset{\lambda g}{prox}(u) = \underset{x}{\operatorname{argmin}} \lambda g(x) + \frac{1}{2}\|x-u\|_2^2. \quad (3)$$

Note that Equation (3) is essentially a denoising problem. Many functions have closed form solutions of their proximal operator. Of special interest in this work is the proximal operator of the $l_1$-norm, which yields the soft-shrinkage operator defined as the point-wise shrinkage function:

$$\tau_{soft}(x,\lambda) = \max\{|x_i|-\lambda, 0\}\operatorname{sign}(x_i) \quad (4)$$

An efficient algorithm to solve Equation (2) that utilizes proximal operations is the iterative shrinkage/thresholding algorithm called ISTA and its accelerated version called Fast-ISTA (FISTA). The algorithm below is derived from the perspective of the majorization-minimization (MM) prescription. MM minimizes a convex surrogate to a function rather than the function itself. Consider a function $Q(\Theta|\Theta^m)$ of $\Theta$ that depends on a fixed parameter $\Theta^m$. Given a function $f(\Theta)$, $Q(\Theta|\Theta^m)$ is said to majorize $f$ at the point $\Theta^m$ if $$Q(\Theta|\Theta^m) \geq f(\Theta) \text{ for all } \Theta, \quad (5)$$

$$Q(\Theta^m|\Theta^m) = f(\Theta^m) \quad (6)$$

The minimizer of the function Q can be shown to descent the function $f$ such that $$f(\Theta^{m+1}) \leq f(\Theta^m) \quad (7)$$

The minimization problem shown in Equation (2) can be split into two functions $f(x)=\frac{1}{2}\|y-Ax\|_2^2$ and $\Phi(x)$. Incorporating this into the MM presecitpion, one can majorize $F:=f(x)+\Phi(x)$ by a first order approximation at a given point $x_k$ with:

$$Q(x|x_k)=f(x_k)+\nabla f(x_k)(x-x_k)=\frac{1}{2}\|x-x_k\|_2^2+\lambda\Phi(x). \quad (8)$$

Q satisfies the conditions in Equations (5) and (6) for a given $x_k$ and with $\lambda \in (0, 1/L]$, where L is a Lipschitz constant of $\nabla f$ and $\Phi(x) \geq 0 \forall x$.

Iteratively minimizing Q yields the IST algorithm:

$$x_{k+1} = \underset{x}{\operatorname{argmin}} Q(x|x_k) \quad (9)$$

$$= \underset{x}{\operatorname{argmin}}\left\{\lambda\Phi(x) + \frac{1}{2}\|x-(x_k-\nabla f(x_k))\|_2^2\right\}.$$

Equation (9) admits the form of Equation (3) with $u=x_k-\nabla f(x_k)$ and thus, the IST algorithm can also be written as:

$$x_{k+1} = \underset{\lambda\Phi}{prox}(x_k - \nabla f(x_k)). \quad (10)$$

If $\Phi=0$, Equation 10 comprises minimizing a smooth convex function and, thus, reduces to the simple gradient method. If $\Phi$ is the $l_1$-norm, $prox_{\lambda\Phi}$ yields the closed form solution given in Equation 4.

ISTA can be further adapted with an accelerated scheme referred to as Fast ISTA or simply FISTA. FISTA includes an extrapolating step in the algorithm:

$$x_{k+1} = \underset{\lambda\Phi}{prox}(z_k - \nabla f(z_k)) \quad (11)$$

$$\tau_{k+1} = \frac{1}{2}\left(1 + \sqrt{1+4\tau_k^2}\right)$$

$$z_{k+1} = x_k + \left(\frac{\tau_k - 1}{\tau_{k+1}}\right)(x_k - x_{k-1}).$$

where the initializers are $\tau 1=1$ and $y=x_0$. Additionally, FISTA can be further generalized in a form referred to as relaxed ISTA where the extrapolation step is expressed as:

$$z_{k+1} = x_k + \gamma_k(x_k - x_{k-1}), \quad (12)$$

and arbitrary $\overset{3}{v}_k$.

The techniques discussed above apply if $\Phi(\cdot)$ is separable. However, in a wavelet based framework, one often encounters $\Phi(x)=\|Wx\|_1$. If W is an orthogonal transform, $\Phi(\cdot)$ is separable and the above techniques can be applied for finding sparse solutions. In practical settings however, orthogonal wavelet transforms lack shift-invariance. In MRI reconstruction this yields to more noise and block artifacts in the reconstructed image compared to undecimated wavelet transforms. On the other hand, undecimated or redundant transforms have higher memory consumption because of the missing decimation step.

DCE MRI

In clinical practice, abdominal dynamic contrast-inhanced (DCE) MRI is performed using multiple breath-hold acquisitions over a period of minutes. In particular iterative reconstruction techniques can provide continuous free-breathing acquisitions with high spatio-temporal resolution into clinical range. This provides patient comfort and robustness, and also aims at quantitative imaging. Some embodiments disclosed herein resolve motion-states as an additional dimension in the image reconstruction. Some embodiments use a Cartesian acquisition strategy with a motion-state detection based on additional navigation scans. The navigation scans are aligned with fat preparation pulses (e.g., frequency selective pulses) and come at practically no time cost. Motion-states are determined by clustering the imaging scans based on those navigation signals, so that imaging scans within a given cluster have navigation signal values closer to each other than to the navigation signal values of imaging scans in other clusters.

A 3D Cartesian spoiled Volume-Interpolated Breath-hold Examination (VIBE) gradient echo (GRE) sequence supporting spectral fat suppression can be extended to support variable-density sampling of the phase-incoding plane as well as the acquisition of a navigation signal as follows:

Some embodiments are suitable for DCE MRI in liver or other tissue. When imaging the liver, the liver is moving during air inhalation and exhalation, because image acquisition is slow (relative to the motion). Motions of the diaphragm are reflected onto the liver during this slow scanning. DCE MRI makes a series of images of the tissue. The series of images captures physical motions and also image contrast changes (due to CA movement into and out from the liver). CS shortens acquisition time per image. CS can allow the patient to breathe freely during acquisition of the sequence of images, because there is little reduction in image quality due to very small motion during the acquisition of a single one of the images. With CS, one can continuously acquire data, and retrospectively exclude data outside of the observation window.

In some embodiments, data acquisition captures data in five dimensions. In addition to three spatial dimensions, time provides a fourth dimension. Because general CA inflow behavior is known empirically, the key points in time for dynamic imaging (relative to CA injection time) can be predicted, and the time is representative of perfusion state. A fifth dimension corresponding to motion states is captured. A clinical application is perfusion where there is CA flowing in, and the intensity of the CA within the body changes. The exemplary methods resolve motion as well as inflow (time domain). For DCE MRI, the time at which the CA is expected to reach tissue (such as the liver) is known empirically, and is an additional significant independent variable for the image resolution.

In some embodiments, given a self-navigation signal in the general form of a sinusoidal curve, the system assigns certain amplitude values of the self-navigation signal to certain motion states, such as inhale and exhale. A simple system can use two motion states for inhalation and exhalation. In other embodiments, additional motion states are used, corresponding to additional positions between maximum inhalation and maximum inhalation.

Figure 2:
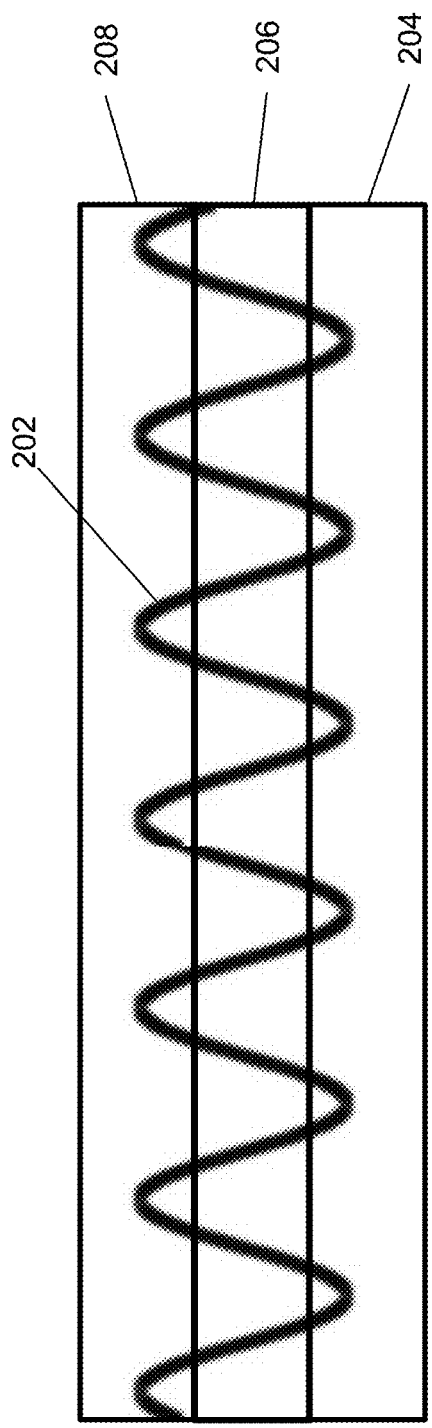
FIG. 2 is a diagram of a navigation signal spanning three amplitude ranges that correspond to three respective motion states of a subject (e.g., a patient).

FIG. 2 shows an example of a gating signal 202, which is representative of breathing motion. A motion signal from the RF coil 12, 14 or 18 can be derived based on similarity of the navigation scans. The navigation scans may be processed before by applying high- and low-pass filtering. The filter settings can be fixed through scan indices and assigned time-points. This is motivated by the fact the navigation signal is always sampled faster than the typical motion (in case of breathing every ~<200 ms) for the high-pass filter, and the time-points are chosen such that low-pass changes (e.g. by injecting contrast agents) do not vary significantly within one time point. For this purpose, a time point (or point in time) refers to a period within a single breathing cycle of a subject being imaged, about 200 ms or less. Similarly typical time-scales can be used. After initial processing every navigation scan can be assigned to a motion state.

The total amplitude range of the signal 202 can be divided into any desired number of ranges, each corresponding to a respective motion state. In some embodiments, each motion state corresponds to a respective cluster of k-space data. For example, in FIG. 2, the amplitude range of the gating signal 202 is divided into three ranges 204, 206 and 208. Range 204 corresponds to maximum inhalation. Range 208 corresponds to maximum exhalation. Range 206 corresponds to intermediate states. This is only one example. Other embodiments can divide the total amplitude range of the signal 202 into 2, 4, 6 or 8 ranges, or any other number to provide a desired precision for the respiratory state data.

For multiple time points, the sampling is generated in ascending order according to a Gaussian distribution, guaranteeing that at each time point the expectation value for acquiring a phase-incoding step differs from its actual acquisition number by at most one. The set of phase-encoding steps is assigned to the echo trains following the fat preparation pulses. For navigation, an additional GRE module is played out after each fat suppression pulse differing from the imaging scans only in the readout. The latter is put in head-feet direction.

The 3D Cartesian data are supplemented with the time dimension and a fifth dimension defining a motion state.

$$X(x,y,z,t) \rightarrow X(x,y,z,t_{DCE},t_{MotionState})$$

Figure 3:
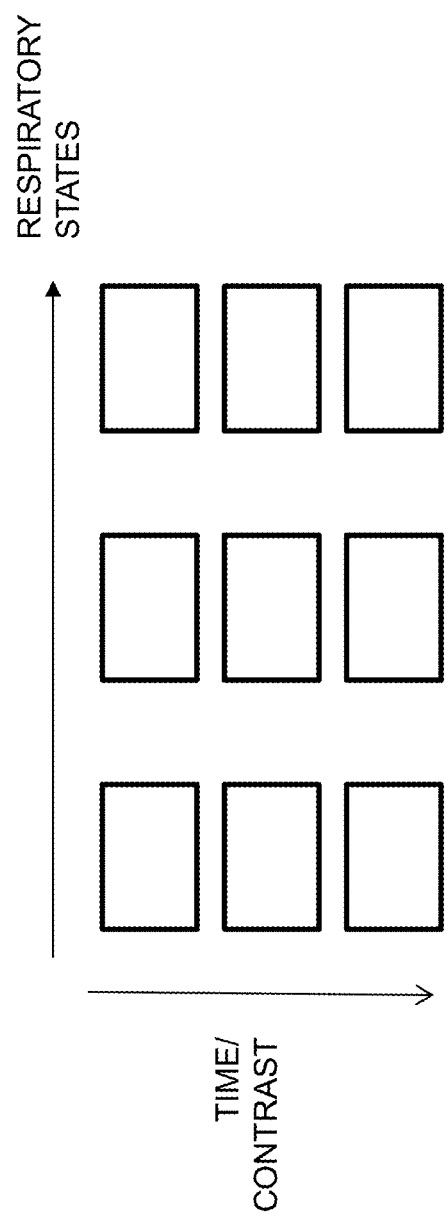
FIG. 3 is a schematic diagram showing a plurality of acquired image data which include two extra dimensions for time and motion (e.g., respiratory motion) state.

For DCE, the time dimension identifies the contrast agent (CA) uptake state. For liver images, the relevant motion state can define diaphragm position. For example, FIG. 3 schematically shows the image data for a given slice (spatial region) is acquired and associated with motion state data from one of three different respiratory states, at three different points in time. Although the example of FIG. 3 has the same number of time points as motion states, any number of time points can be used, independent of the number of motion states.

Figure 4:
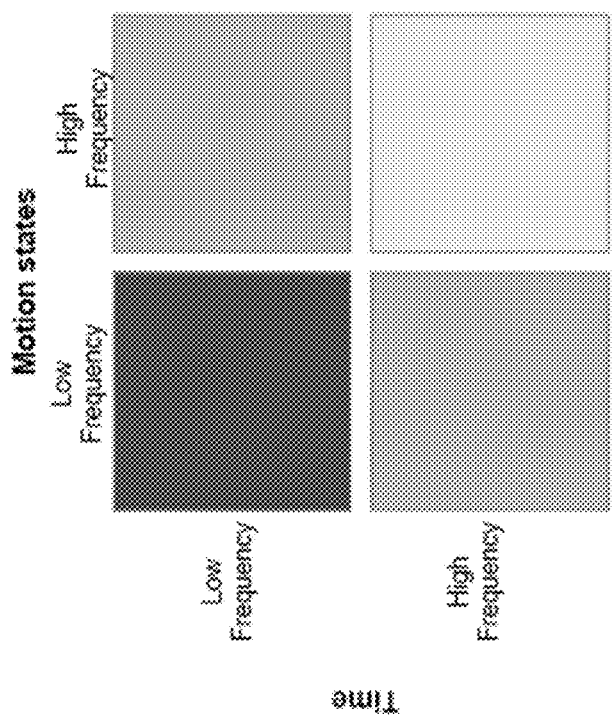
FIG. 4 is a schematic diagram showing the bands of wavelet coefficients for the MR k-space data.

FIG. 4 is a schematic diagram showing the Wavelet coefficients, representing the signals in the wavelet domain. The blocks in FIG. 4 represent "bands" in the wavelet domain. The upper left corner band represent the low frequency component in the time direction and low frequency component in the motion state direction. The upper right corner band represents the low frequency component in the time direction and high frequency component in the motion state direction. No matter how many time points or motion states are included in the k-space data, after a wavelet transform along the two dimensions, the wavelet coefficients can be categorized into these four bands.

Regularization applied on all spatial, DCE and motion-state directions, with different regularization levels, using.

$$x = \operatorname{argmin} \frac{1}{2}\|y - F_u x\|^2 + \sum_i \lambda_i |W_i x|_1$$

The extra respiratory motion-state dimension is used to disentangle dynamic contrast enhancement and respiratory motions. Additional data are acquired for a small liver dome region showing how the diaphragm is moving to directly image respiratory motion. FIGS. 5A-5D show a sample of the navigation signals from which the motion states are obtained.

Some embodiments acquire the navigating signal together with k-space data, compute motion states, cluster the k-space data according to motion state of the navigation signal and label each acquired k-space data with the corresponding motion state, and then decide how to use this data. In the case of acquired data acquired outside of the relevant window, the system does not discard the data, but suppresses their relevance.

The method concatenates image data into large 4D or 5D cube. The 4D cube includes 2D spatial data, plus time and motion state. The 5D cube includes 3D spatial data, plus time and motion state. Regularization is performed on the 4D or 5D cube. During reconstruction, the images may be adjusted to try to make images corresponding to neighboring motion states look similar to each other. Each motion state should be a faithful representation of its data, while at the same time, adjacent motion states should be similar to each other. This is done by applying wavelet transform over the entire 4D or 5D cube of data. It's 5D, but sometimes it is reconstructed as 2D or 3D spatial, plus time, plus motion state.

Using a generalized k-means algorithm, the navigation signal is clustered into N motion-states by minimizing $$\min_{\{C_{c,r}\},\{m_{c,r}\}} \left( \sum_{c=1}^{N} \sum_{r=1}^{R} \sum_{i \in C_{c,r}} |S_{i,r} - m_{c,r}|^2 + \alpha \sum_{c=1}^{N} \sum_{r=1}^{R-1} |m_{c,r+1} - m_{c,r}|^2 \right),$$

with $S_{i,r}$ being the $i^{th}$ navigation scan at the $r^{th}$ time point. C is a motion state, i is a scan index, r is a time index, m is a mean motion state, N is a number of motion states, R is the number of points in time, $S_{i,r}$ is a value of the navigation signal data for an $i^{th}$ navigation scan at an $r^{th}$ point in time. Alpha ($\alpha$) is a tuned parameter that regulates whether centroids within a time-point are determined for each time point separately ($\alpha=0$) or whether the same centroids are used for all time-points ($\alpha=$infinity). In some embodiments, $\alpha$ is set to 0.1 for reconstruction. FIG. 5A shows an example of a navigation scan signal. The optimization is performed for each coil element 12, 14, and 18, and the configuration yielding the best relative improvement compared to the accumulated variance is selected. The obtained motion-states $\{C_{c,r}\}$ are sorted and assigned to the whole respective echo train. The navigation signal is obtained practically without loss in acquisition time as dummy scans and/or inversion time are conventionally put between fat preparation and imaging scans. As a result, the imaging scans D(k,r,i) are indexed by k-space, time point and motion-state. The corresponding 3d+time+motion-state image volumes I(x,r,i) are reconstructed by optimizing (i.e., finding the minimum value of the quantity):

$$\min_I (\|FI - D\|_2^2 + \lambda \|WI\|_1),$$

with W being a redundant wavelet transformation (e.g., Haar or Debauchies), $\lambda$ the regularization strength and F consisting of multiplication with coil-sensitivities, Fourier transformation and masking.

In addition a reconstruction using a fixed gating acceptance for a single motion-state (referred to as hard-gating) provides a basis for comparison with soft-gating as described herein. In some embodiments, the system displays a second image reconstructed using the fixed gating signal adjacent to at least one image reconstructed using the motion state data, such as shown in FIGS. 6B, 7A and 7B. The optimization problem above is then modified to finding the best subset of given size at each time point.

FIGS. 6A and 6B show how the soft-gating described herein compares to the hard gating approach In FIG. 6A, the hard gating data 602 are indicated by squares, and can be provided by a sensor attached to a band around the patient's abdomen to detect maximum exhalation and inhalation, for example. The hard gating data 602 show a local maximum CA concentration at time 10. The XD VIBE data 604 reflecting both time and motion state dimensions is indicated by asterisks. At time 8 in FIG. 6A—corresponding to the arterial phase—the XD VIBE data 604 include a global maximum CA concentration due to inflow-outflow behavior, which is not detected by hard gating data 602.

FIG. 6B shows the reconstructed images for the same slice based on hard gating (left) and XD VIBE with time and motion state (right). The XD VIBE image has greater contrast and less noise.

Experiments

A DCE-MRI scan of the liver was performed in free breathing on a clinical 3T scanner (MAGNETOM Skyra, Siemens Healthcare, Erlangen, Germany). Parameters of the VIBE acquisition included FoV=380×345×192 mm3, image matrix=320×290×64, TE/TR=1.8/3.76 ms, flip angle=10°, 6-fold acceleration in the phase-encoding with the probability distribution of the variable sampling at the borders dropping to ⅕ of its central value as well as 16 time points with a temporal resolution of 11,57s each. Reconstruction was performed using a C++ prototype for the case of 6 motion-states and for a gating acceptance of 40%, respectively. FIGS. 5A-5D show the navigation signal used during this experiment.

FIG. 5A shows the separate navigation signal $S_{i,r}$ from one of the coils 12, 14, 18 during a navigation scan performed between fat preparation and imaging scans. The navigation signal data are to be used to label the k-space data. The coils 12, 14 and 18 are at different locations in the head-to-foot (Z) direction. The horizontal axis in FIGS. 5A-5D represents time. Each column in FIG. 5A represents 1 image. The X-axis is the time coordinate for the image at different times.

The acquired navigation signal $S_{i,r}(z)$ (FIG. 5A) corresponds to projections in head-feet direction with the same excitation volume as the imaging scans. In FIG. 5A, there is a dark band 501 above a white band 503. The white band 503 is the signal representing liver motion state, and the dark band 501 above it represents the diaphragm motion state, as the liver moves up and down. In the third column 505, the navigation data shows that the liver is moving down significantly and comes back up, corresponding to movement of the diaphragm.

FIG. 5B shows the phase of the navigation signal $S_{i,r}$ of FIG. 5A as a function of time for a selected coil element 12, 14 or 18. The signal shows variation due to breathing motion, and the method will align the phase with the breathing motion.

The signal for the selected coil element is binned into 16 time points, assigned motion indices for 6 motion-states as well as clustering according to motion index for each time point, separately. FIG. 5C shows the motion state of the navigation signal Si,r. The course of the motion state shows clear periodic motion that may be attributed to motion of the liver and which is most extreme during contrast injection at the 3rd time point.

FIG. 5D shows the clustering of the navigation signal for 6 motion-states as well as a sorting according to motion-states for each time point.

Reconstructed images close to the liver dome are shown in FIGS. 7A and 7B. FIG. 7A shows the first 6 time points are shown in respective columns 1 to 6 for a slice close to the liver dome using a hard-gated reconstruction with a gating tolerance of 40%. FIG. 7B shows a motion-resolved reconstruction with 6 motion-states ranging from inhalation to exhalation. For brevity, only the even-numbered motion states are shown, but the odd-numbered motion states can be reconstructed in the same manner. The hard-gated reconstruction (FIG. 7A) shows good results at time points with moderate motion and signal change. However, at time point 3 with contrast agent arrival and stronger breathing motion, the motion-resolved reconstruction (FIG. 7B) provides better image quality than the hard gated reconstruction (FIG. 7A) for the exhaled state. The motion-resolved reconstruction (FIG. 7B) also shows fewer vessels at later time points which indicates less blurring in the through-plane direction.

The techniques described herein permit free-breathing liver DCE for Cartesian acquisitions when imaging scans are clustered according to motion-states. Reconstruction times and image volumes scale at least linear in the motion-states. Other embodiments include a variable number of motion-states or a combination with hard-gating.

Figure 10:
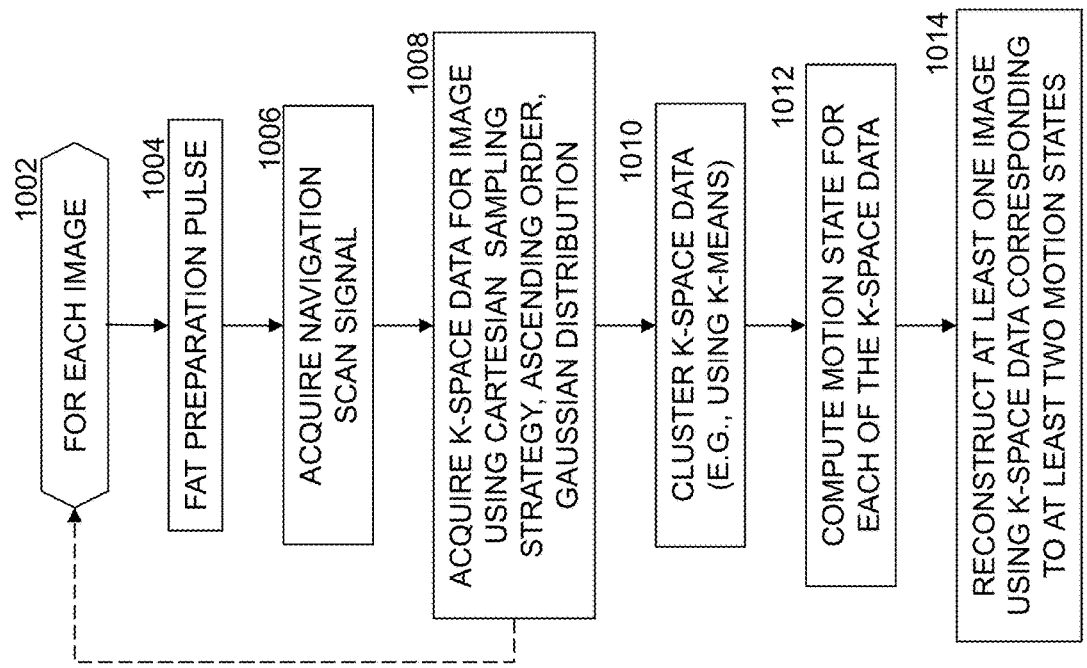
FIG. 10 is a flow chart of an exemplary MRI method according to some embodiments.

FIG. 10 is a flow chart of an exemplary XD VIBE method as described above.

At step 1002, a loop including steps 1004 to 1008 is performed for each image.

At step 1004, a fat suppression technique, such as a fat preparation pulse is performed. In various embodiments, the fat suppression method can include difference in resonance frequency with water by means of frequency selective pulses, phase contrast techniques, short T1 relaxation time by means of inversion recovery sequences (STIR technique), a so-called Dixon method, or a hybrid technique combining two or more of these fat suppression techniques such as SPIR (spectral presaturation with inversion recovery).

At step 1006, the navigation signal data for the image are acquired. In some embodiments, for imaging the liver, the navigation signal has a frequency band corresponding to motion of the patient's diaphragm. In other embodiments, the navigation signal corresponds to a frequency band corresponding to motion of the patient's heart.

At step 1008, the k-space data for the image are sampled using a Cartesian trajectory. In some embodiments, the k-space data are acquired in ascending order according to a Gaussian distribution.

At step 1010, the k-space data are clustered using a clustering method, such as a k-means algorithm.

At step 1012, the motion state for each of the k-space data are computed based on the clustering. Each of the k-space data is labeled with its corresponding motion state.

At step 1014, at least one image is reconstructed using k-space data corresponding to at least two motions states corresponding to the same point in time. In some embodiments, at least one image is reconstructed using k-space data corresponding to all of the motions states corresponding to the same point in time.

Extra Dimension (XD) Hybrid

In some embodiments, as described above, the system reconstructs images using data from all motion states at multiple time points. In other embodiments, the system uses a first number of motion states for reconstruction at certain time points, and uses a second number of motion states for reconstruction at other time points, where the first number and second number are different from each other. For example, in some embodiments, referred to herein as the XD hybrid approach, the system only performs full motion state resolution for certain time points, and performs resolution for a single motion state at the remaining time points. For example, in some embodiments, a first image is reconstructed from k-space data corresponding to a first number of motion states acquired at the first time, and a second image is reconstructed from k-space data corresponding to a second number of motion states acquired at the second time, where the second number is different from the first number.

For example, given a 2 min. scan, the system can perform full motion state resolution every 10 seconds, and the image is resolved for a single motion state at the remaining time points.

FIG. 8 is a schematic diagram showing the data used during image reconstruction in some embodiments of the XD Hybrid method. The gray boxes 801, 804, 807 indicate data from different points in time corresponding to a first motion state. The second row of boxes 804, 805, 806 in FIG. 8 corresponds to a predetermined critical time (e.g., when the CA arrives at the liver) when the CA concentration is expected to be greatest, based on empirical knowledge of CA inflow/outflow. At the predetermined time corresponding to the second row, extra data (indicated by black boxes) 805, 806 corresponding to additional motion states are used to reconstruct the image, for better image quality. For the remaining points in time, the images for the first motion state (gray boxes 801, 807 can be processed using only the data from a single image.

According to this embodiment of an XD Hybrid method, the final image for a critical time and desired motion state is obtained from:

$$\min_{x_{t \cup m}}(\|y - AX_{t \cup m}\| + \lambda_t \|\psi_t X_t\| + \lambda_m \|\psi_m X_m\|), \text{ where:}$$

$X_t$=2D+t data at desired motion state
$X_m$=2D+motion states (+t) data at arterial phase(s)
$X_{t \cup m}$=2D data at arterial phase(s) and the desired motion state; the average of $X_t$ and $X_m$ at each iteration
$\psi_t$=3D wavelet transform. Thresholding scale along t.
$\psi_m$=3D (or 4D) wavelet transform. Thresholding scale along motion (and t if multiple arterial phases)

Figure 9:
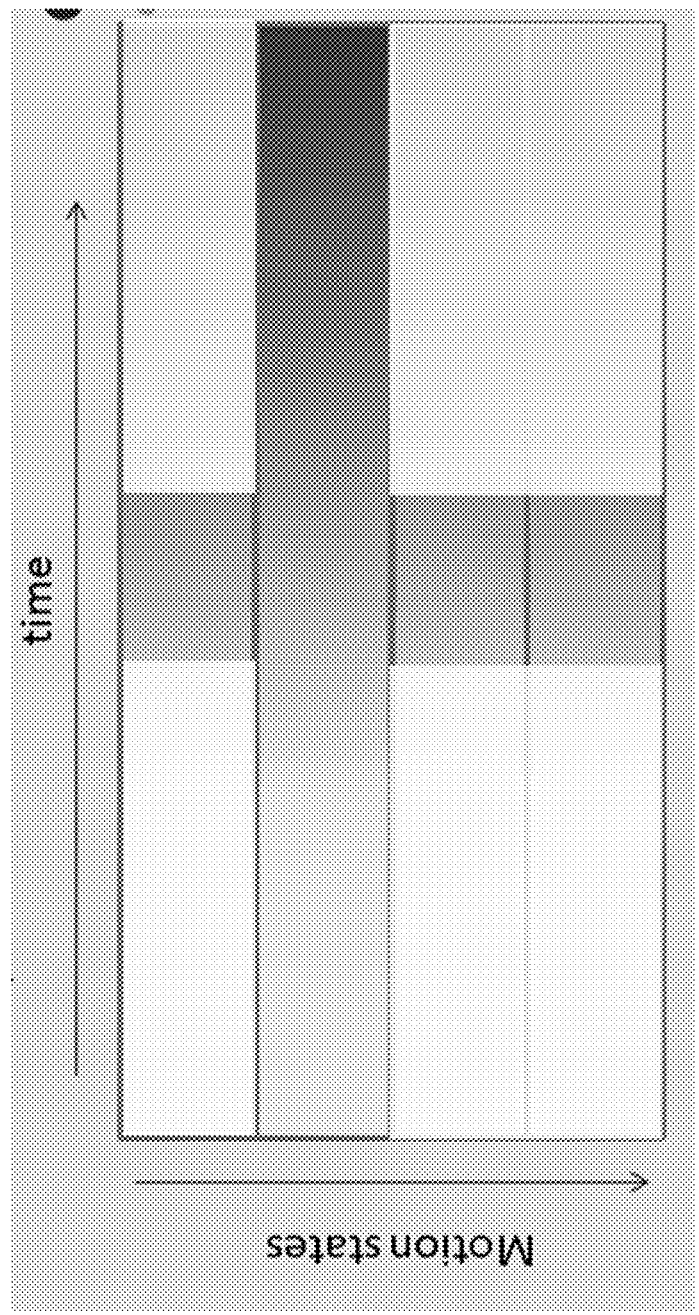
FIG. 9 is a schematic diagram of a generalized method using the XD Hybrid technique of FIG. 8.

Although FIG. 8 shows an example in which only three points in time and three motion states are considered, any number of points in time and any number of motion states can be used. FIG. 9 is a more general schematic diagram, in which an XD Hybrid embodiment can use any number of points in time, and any number of motion states to reconstruct an image at a critical point in time for a desired motion state.

Figure 11:
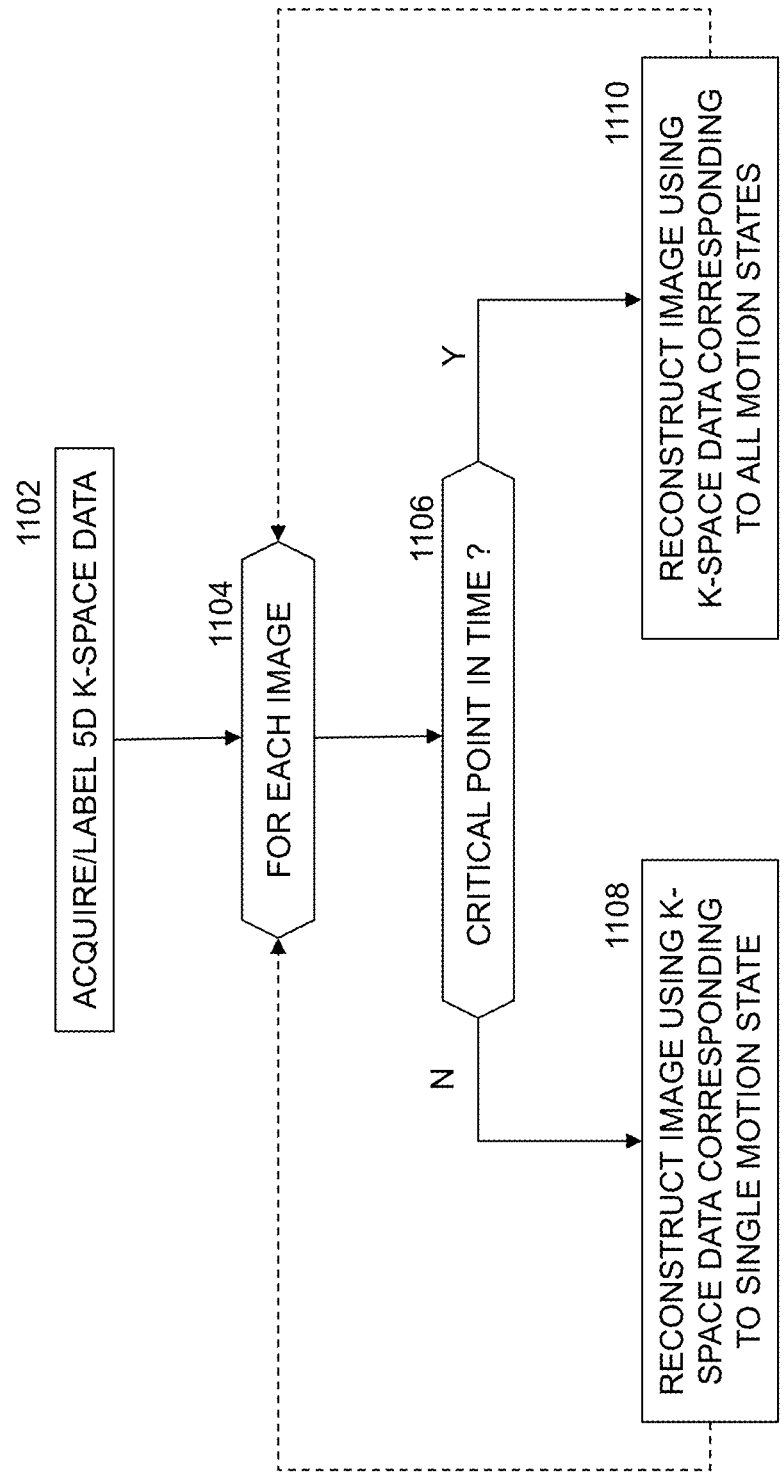
FIG. 11 is a flow chart of an XD Hybrid method according to some embodiments.

FIG. 11 is a flow chart of an exemplary XD Hybrid method according to some embodiments.

At step 1102, the 5D k-space data are acquired and labeled as described above with respect to FIG. 10.

At step 1104, a loop including steps 1106-1110 is repeated for each image.

At step 1106, a determination is made whether the image corresponds to a critical point in time. For example, in a perfusion study, a time corresponding to a maximum concentration of a CA in the tissue being imaged is a critical point in time. If the image corresponds to a critical time, step 1110 is executed. If the image does not correspond to a critical time, step 1110 is executed.

At step 1108, the image is reconstructed using k-space data corresponding to a single motion state at multiple points in time, to increase performance.

At step 1110, the image is reconstructed using k-space data corresponding to all of the motion states acquired at that same point in time, to increase image quality.

The XD Hybrid method provided improved image quality at critical points in time, and improved image reconstruction time for images acquired at non-critical points in time.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method comprising:
   acquiring navigation data during navigation scans at each of a plurality of points in time;
   acquiring a plurality of magnetic resonance imaging (MRI) k-space data corresponding to an imaged object at the plurality of points in time using Cartesian sampling, the k-space data including at least two spatial dimensions, a time, and a motion state;
   computing the respective motion state for each of the k-space data based on the navigation data; and
   reconstructing at least one image from the plurality of MRI k-space data using k-space data corresponding to at least two motion states and the same point in time to reconstruct the at least one image,
   wherein each of the plurality of points in time corresponds to a respective imaging scan, and the step of acquiring navigation data is performed between a fat preparation pulse and a respective one of the imaging scans at a respective point in time.

2. The method of claim 1, further comprising clustering the k-space data according to navigation data using a k-means method.

3. The method of claim 2, wherein the clustering computes:

$$\min_{\{C_{c,r}\},\{m_{c,r}\}} \left( \sum_{c=1}^{N} \sum_{r=1}^{R} \sum_{i \in C_{c,r}} |S_{i,r} - m_{c,r}|^2 + \alpha \sum_{c=1}^{N} \sum_{r=1}^{R-1} |m_{c,r+1} - m_{c,r}|^2 \right),$$

where C is a motion state, i is a scan index, r is a time index, m is a mean motion state, N is a number of motion states, R is the number of points in time, $S_{i,r}$ is a value of the navigation data for an $i^{th}$ navigation scan at an $r^{th}$ point in time.

4. The method of claim 1, wherein each imaging scan has an excitation volume, and the navigation scans have a same excitation volume as the imaging scans.

5. The method of claim 1 wherein the sampling is generated in ascending order according to a Gaussian distribution for the plurality of points in time.

6. The method of claim 1, wherein the object is a patient, the navigation data is acquired from a coil near a diaphragm of the patient, and the at least one image is an image of a liver of the patient.

7. The method of claim 1, further comprising providing a fixed gating signal for a single motion state, and displaying a second image reconstructed using the fixed gating signal adjacent to the at least one image.

8. The method of claim 1, wherein:
   the plurality of points in time include a first time and a second time,
   the at least one image includes a first image reconstructed from k-space data corresponding to a first number of motion states acquired at the first time, the method further comprising:
   reconstructing a second image from k-space data corresponding to a second number of motion states acquired at the second time, wherein the second number is different from the first number.

9. The method of claim 8, wherein the object is a liver of a patient, and a contrast agent flows into the liver at the first time.

10. The method of claim 8, wherein the first image is reconstructed using k-space data corresponding to all of the motion states.

11. A system comprising:
    a magnetic resonance (MR) imaging device having a plurality of coils, and configured to collect data representing an MR image from an object;
    a processor having a storage device for storing frequency components of the data acquired using a Cartesian acquisition strategy during acquisition of the frequency components, the processor programmed for:
    acquiring navigation data during navigation scans at each of a plurality of points in time;
    acquiring a plurality of magnetic resonance imaging (MRI) k-space data corresponding to an imaged object at the plurality of points in time using Cartesian sampling, the k-space data including at least two spatial dimensions, a time, and a motion state;
    computing the respective motion state for each of the k-space data, based on the navigation data;
    reconstructing at least one image from the plurality MRI k-space data using k-space data corresponding to at least two motion states and the same point in time to reconstruct the at least one image; and clustering the k-space data according to the navigation data using a k-means method, wherein each of the plurality of points in time corresponds to a respective imaging scan, and the processor is programmed to acquire navigation data between a fat preparation and a respective one of the imaging scans at a respective point in time.

12. The system of claim 11, wherein the processor is programmed for displaying a second image reconstructed using the fixed gating signal adjacent to the at least one image.

13. The system of claim 11, wherein the processor is programmed for:

reconstructing the at least one image from k-space data corresponding to two or more motion states acquired at a first time, and reconstructing a second image from k-space data corresponding to a single motion state acquired at a second time.

14. A non-transitory machine-readable storage medium encoded with computer program code, wherein when a processor executes the computer program code, the processor performs a method comprising the steps of:

acquiring navigation data during navigation scans at each of a plurality of points in time;

acquiring a plurality of magnetic resonance imaging (MRI) k-space data corresponding to an imaged object at the plurality of points in time using Cartesian sampling, the k-space data including at least two spatial dimensions, a time, and a motion state;

computing the respective motion state for each of the k-space data based on the navigation data; and reconstructing at least one image from the plurality MRI k-space data using k-space data corresponding to at least two motion states and the same point in time to reconstruct the at least one image, wherein the sampling is generated in ascending order according to a Gaussian distribution for the plurality of points in time.

15. The non-transitory machine-readable storage medium of claim 14, wherein the processor is further programmed for providing a fixed gating signal for a single motion state, and displaying a second image reconstructed using the fixed gating signal adjacent to the at least one image.

16. The non-transitory machine-readable storage medium of claim 14, wherein the processor is programmed for:

reconstructing the at least one image from k-space data corresponding to two or more motion states acquired at a first time, and reconstructing a second image from k-space data corresponding to a single motion state acquired at a second time.

17. The non-transitory machine-readable storage medium of claim 14, wherein the first image is reconstructed using k-space data corresponding to all of the motion states.

* * * * *